US00PP11728P2

(12) United States Plant Patent
Osiecki

(10) Patent No.: US PP11,728 P2
(45) Date of Patent: Jan. 2, 2001

(54) ANTHURIUM PLANT 'A4'

(75) Inventor: Marian W. Osiecki, Marianna, FL (US)

(73) Assignee: Oglesby Plants International, Inc., Altha, FL (US)

( * ) Notice: Under 35 U.S.C. 154(b), the term of this patent shall be extended for 0 days.

(21) Appl. No.: 09/239,150

(22) Filed: Jan. 28, 1999

(51) Int. Cl.[7] ..... A01H 5/00
(52) U.S. Cl. ..... Plt./365
(58) Field of Search ..... Plt./369, 365

*Primary Examiner*—Howard J. Locker
*Assistant Examiner*—Michelle Kizilkaya
(74) *Attorney, Agent, or Firm*—Rothwell, Figg, Ernst & Manbeck

(57) ABSTRACT

A new and distinct cultivar of Anthurium is provided. It is a medium to large size plant, suitable for production in 15 cm to 25 cm pots from a single tissue culture produced microcutting with vigorous growth, early and abundant branching, early, year — round and abundant flowering. Striking, bright red, very glossy spathes are carried on strong peduncles slightly above foliage and sharply contrast with light colored spadixes and with dark green, thick leaves.

2 Drawing Sheets

SUMMARY OF THE INVENTION

This invention relates to a new and distinct Anthurium cultivar characterized by the following combination of repeatedly observed traits:

1. Medium to large size plant,
2. very vigorous growth,
3. large, thick, leathery, dark green leaves,
4. early, year—round and abundant flowering,
5. prominent, relatively large, bright red, very glossy spathes held slightly above foliage on strong peduncles,
6. light colored spadixes, sharply contrasting with spathes and primarily selected for those characteristics being so selected from the progeny of the cross stated below being grown near Altha, Fla. in a cultivated area.

ORIGIN AND ASEXUAL REPRODUCTION

Asexual reproduction of this cultivar by tissue culture was directed by me. The reproduction establishes that the plant does in fact maintain the characteristics described in successive generations.

The plant was initially selected where grown in a planned breeding program in or near Altha, Fla. and has been reproduced by tissue culture in the vicinity of Altha, Fla. since 1992 with the characteristics stated. The female parent was a selected clone of Anthurium 'Ruth Morat' U.S. Plant Pat. No. 8,540, a/k/a Lady Ruth™ and the male parent was a selected *Anthurium andreanum* seedling designated "AR 891" (patent not applied for). The cross was made in 1991 and the seedling was selected in 1992.

This new cultivar has been identified as Anthurium 'A4'. It is possible that other identification will be adopted in the trade but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'A4' was approximately 15 months from planting a single tissue culture produced microcutting and was grown in a 15-cm pot.

In the photographs:

DETAILED DESCRIPTION OF THE NEW CULTIVAR

Figure 1:
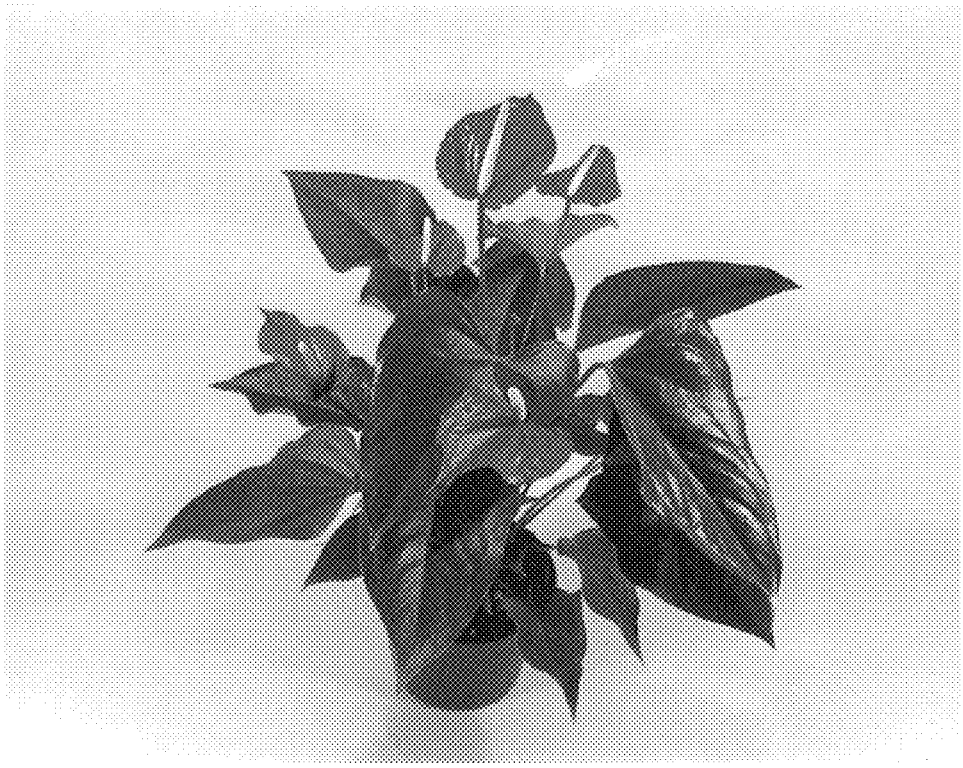
FIG. 1 depicts the whole plant.
Figure 2:
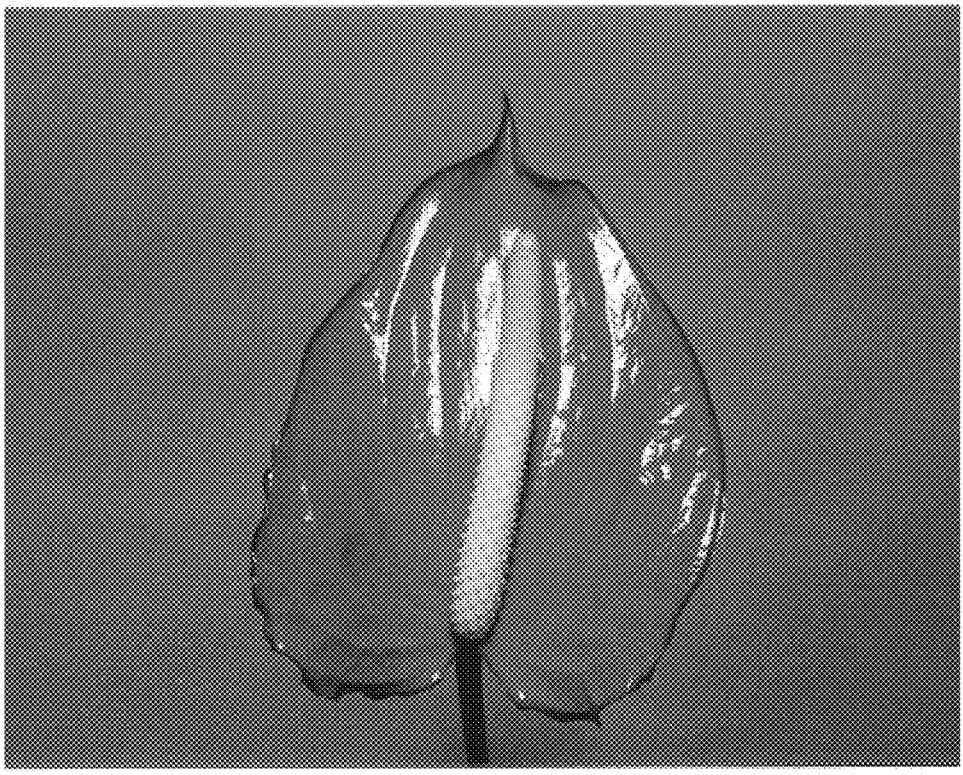
FIG. 2 illustrates the mature inflorescence.
Figure 3:
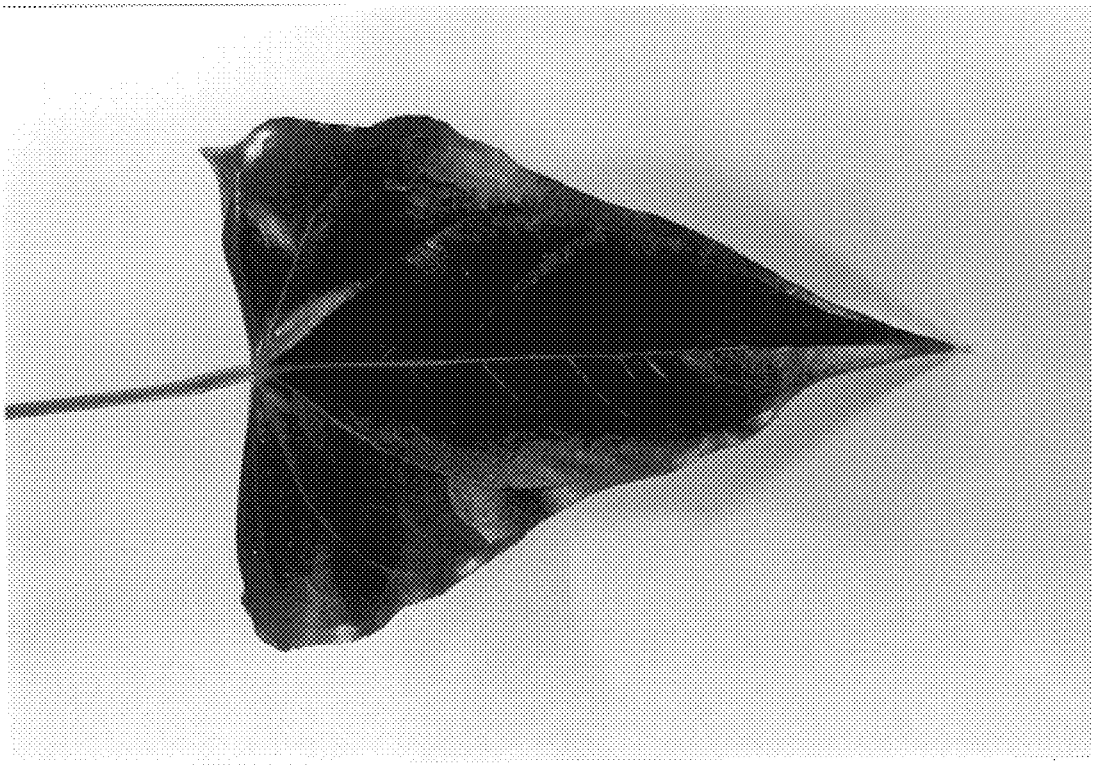
FIG. 3 illustrates the top of a mature leaf.
Figure 4:
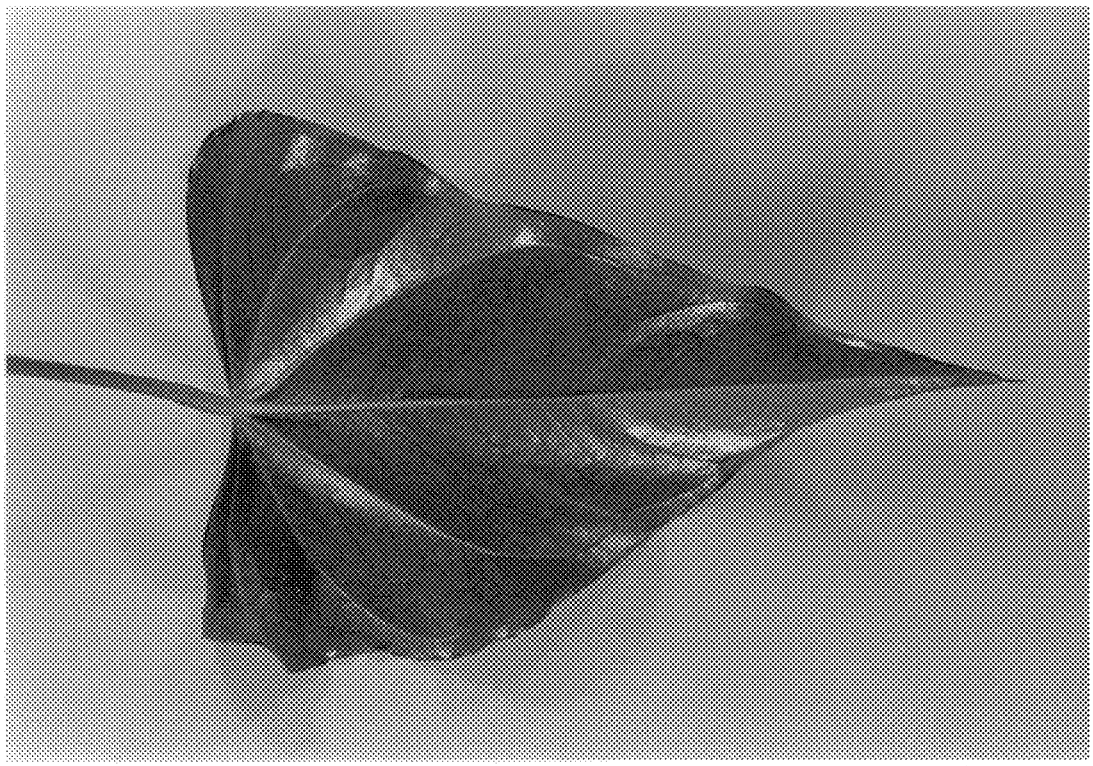
FIG. 4 illustrates the bottom of a mature leaf.

The following observations and measurements describe plants grown near Altha, Fla. under greenhouse conditions. These observations and measurements were recorded in November 1998 from mature plants in 15 cm pots, about 14 months from planting a single tissue culture produced microcutting per pot. Fully developed organs on a main stem were used for measurements and color description, unless otherwise indicated. Color values were determined on Nov. 12 and 13, 1998 under natural, indirect light of approximately 550–1300 foot-candles. Color references are made to The R.H.S. Colour Chart, except where general color terms of ordinary significance are used.

'A4' has not been observed under all possible environmental conditions. The phenotype may vary with variations in environment and horticultural practices such as temperature, light intensity, day length, fertilization, propagation procedure etc., without any change in genotype.

Botanical classification: Anthurium hybrid cultivar A4.
Parentage:

*Female parent.*—Selected clone of Anthurium 'Ruth Morat' (U.S. Plant Pat. No. 8,540, a/k/a Lady Ruth™).

*Male parent.*—Selected *Anthurium andreanum* seedling designated "AR 891" (not patented).

Propagation: Plant tissue culture.
Plant descriptions:

*Growth habit.*—Medium to large size, well branched, relatively full.

*Height.*—Foliage 29.5–41.0 cm; with spathes 34.5–40.5 cm.

*Width.*—48.0–57.0 cm.

Petiole.

*Size.*—17.2–20.6 cm long, 3.6–4.3 mm in diameter below geniculum.

*Geniculum.*—2.0–2.5 cm long, 4.5–6.0 mm in diameter at the base; sometimes petiole slightly bends at the base of geniculum.

*Petiole wings.*—2.2–4.2 cm long.

*Color.*—Geniculum: Adaxial: Resembling 144A distally and 146A–B proximally (both yellow-green); sometimes a trace of greyed-orange or greyed-red present in the central shallow groove. Abaxial: 144A–B. Below geniculum: Adaxial: 146A–B immediately below geniculum; proximally becomes slightly darker (at the wings tip most similar to 146A). Abaxial: Immediately below geniculum 144A; proximally becomes gradually darker—similar to 146A near base; various amounts of greyed-orange sometimes present on the base. Petiole wings: 146A–C (yellow-green), sometimes with some greyed-orange or greyed-red. Young leaves' petioles tend towards grey-brown (similar to 199A).

Leaf blade:

*Shape.*—Ovate; tip acuminate with some aristate tendencies, sometimes slightly asymmetric; base truncate with some cordate tendencies, which increase with plant age, often slightly asymmetric. Lobes usually slightly curved upwards. Margin slightly wavy.

*Size.*—17.7–21.3 cm long, 12.8–15.6 cm wide; length:width ratio 1.3–1.4:1.

*Texture.*—Thick, leathery, smooth, semiglossy; young leaves highly polished.

*Veins.*—Prominent near the base, less conspicuous near the tip.

*Color.*—Newly unrolled leaf: Early, between yellow-green and grey-brown on both sides, with adaxial side tending more toward yellow-green and abaxial side tending more toward grey-brown. Abundant brown color (similar to 200A–C) on both sides is sometimes present. Later, the adaxial side becomes darker than 146A and abaxial side becomes similar to 148A (both yellow-green). Margin is greyed-purple and primary veins on both sides are light greyed-purple. Mature leaf: Adaxial: Darker than 147A (yellow-green). Most of midrib and proximal portions of primary veins lighter than the surrounding tissue, similar to 146B and 144A (both yellow-green). Abaxial: Similar to 146A, but also resembling 147B, especially in aging leaves. Veins similar to 144A, especially in proximal half.

SCALE LEAVES

Covering lateral bud penultimate to the mature inflorescence:

*Length.*—7.5–8.8 cm.

*Color.*—(Abaxial): Young leaf scales are greyed-purple (similar to 184A–B) with yellow-green tips and variable amounts of yellow-green on the midrib and in longitudinal streaks on both sides of the midrib; slightly translucent; eventually becoming more pale and grey-brown before senescing.

Between peduncle of young inflorescence and stem:

*Length.*—3.2–4.3 cm.

*Color.*—(Abaxial): greyed-purple (similar to 184B–D) with variable amounts of yellow-green on two protruding ribs and in some longitudinal streaks; translucent.

Inflorescence:

*Arrangement.*—Mature spathes usually situated slightly above foliage, approximately horizontal or slightly oblique with tips pointing upwards; spadix at approximately 40–55° angle with spathe's midrib; approximately 3–4 mm of peduncle between spathe and spadix base in front; no stipe. Ratio spathe length:spadix length 1.6–1.7:1.

Peduncle:

*Size.*—25.0–31.2 cm long, 3.9–4.8 mm in diameter immediately below spathe.

*Color.*—Front: Red between spathe base and spadix base, similar to or a little lighter than spathe. Greyed-red (approximately 178A–B) and greyed-orange (approximately 176A–B, 166A–B) colors present immediately below spathe merge proximally with yellow-green (approximately 144A), which is the most prevalent color. Back: In the most distal approximately 3 cm colors gradually merge from the red color of the spathe to greyed-red (approximately 178A–B) and/or greyed-orange (approximately 166A–B) to yellow-green (approximately 144A).

Spathe:

*Shape.*—Ovate, usually almost flat at maturity; tip acuminate with aristate tendencies and with edges rolling frontward; base cordate, often slightly asymmetric; lobes extend 8–12 mm past peduncle; margin wavy, especially near base.

*Size.*—7.8–10.9 cm long, 7.4–8.8 cm wide; length:width ratio 1.0–1.2:1.

*Texture.*—Smooth, leathery, highly polished with variable degree of puckering.

*Color.*—Bud: Varies between 45A and 46A (both red). Newly unrolled spathe: Front: Darker than 46A. Back: 53A–B (red) with yellow-green tip. Mature spathe: Front: Similar to 46A or slightly lighter. Back: 53B–C (red) with yellow-green tip. A greyed-purple (approximately 185A) band, approximately 1 mm wide is present along the margin on both sides of young and mature spathes. Spathe retains red color for at least two months following appearance of bud above or among leaves.

Spadix:

*Shape.*—Columnar, slightly tapering at tip.

*Size.*—4.8–6.4 cm long; 7.7–8.2 mm in diameter.

*Flower density.*—Approximately 14–15 flowers per linear 2-cm in mid-portion of spadix.

*Color.*—Young inflorescence with newly unrolled spathe and no visible pistils: Yellow-orange (resembling 22B–C and 23C) with red dots, from which pistils eventually protrude. Mature inflorescence with pistils visible on at least ¾ of spadix: Proximal zone orange-white (159C), often with pale red marks adjacent to pistils. On some spadixes various areas in proximal half are pink and/or yellow. Distal zone without pistils varies from yellow-orange (similar to 22A or 23B) with inconspicuous red dots to orange-red (approximately 30D), distally becoming darker and more red (approximately 31B). Tip often resembles all or some of the following orange-red colors: 31A–B, 32B, 34C, 35B.

Botanical flower:

*Perianth.*—Prominent between small pistils. Perianth of an individual flower appears on the spadix surface as almost a diamond shape, approximately 3.0 mm long and 2.5–3.0 mm wide.

*Pistil.*—Approximately 2 mm long, 1 mm in diameter; protrudes fraction of a mm beyond perianth, white, translucent, especially in proximal part. Stigma minute.

*Stamen.*—Approximately 1.2–1.5 mm long, 0.8–1.0 mm wide, white, translucent, not visible at flower maturity. Anther protrudes slightly beyond perianth at the time of pollen release.

*Pollen.*—Moderate amounts of white pollen produced. Spontaneous seed production very rare.

Flowering: Flowers naturally in 12.5 cm pots, about 9–11 months from planting tissue culture produced microcuttings. Continuous year — round flowering. At approximately 14 months four to six spathes are visible above and among leaves.

ROOTS

Roots above soil level — few, thick, fleshy, non-branching; young aerial roots are greyed-orange and greyed-red with some grey-brown and with yellow root caps. Old aerial roots grey-brown to grey with yellow root caps and sometimes some greyed-red proximally from the cap.

Strong root system below soil level; primary roots thick, fleshy, cream to greyed-yellow with variable pink areas and with yellow root caps. Numerous secondary roots lighter in color to almost white with yellow root caps.

DISEASE AND INSECT RESISTANCE

No unusual susceptibility to diseases or insects noted to date.

COMPARISON WITH THE KNOWN CULTIVARS

The new cultivar can be compared to the known Anthurium cultivars: 'Ruth Morat' U.S. Plant Pat. No. 8,540 a/k/a Lady Ruth™, '75-10' U.S. Plant Pat. No. 9,355 a/k/a Red Hot™, 'A8' U.S. Plant Pat. No. 10,551 a/k/a Nicoya™ and 'A7' U.S. Plant Pat. No. 10,747 a/k/a Kingston™. The comparisons were made on plants grown under similar conditions in a greenhouse near Altha, Fla.

'A4' is distinguished from all four cultivars by light colored spadixes, which have greater contrast with brighter red and more puckered spathes.

'A4' is further distinguished from 'Ruth Morat' by its larger size; fuller growth habit; more vigorous growth; earlier and more abundant branching; earlier and more abundant flowering; more truncate (less obtuse) leaf bases; by its darker, glossier and much larger spathes, held higher above foliage on thicker, stronger peduncles.

'A4' is further distinguished from '75-10' by its larger size; less abundant flowering; better quality of first inflorescences; slightly lighter foliage; by its wider leaf blades with more truncate (less cordate) bases; predominantly green petioles and peduncles; darker, much larger and glossier spathes, usually held closer to foliage.

'A4l ' is further distinguished from 'A8' by its more truncate (less cordate) leaf blades; darker petioles, peduncles and young leaf blades; darker spathes; shorter ornamental value of inflorescences.

'A4' is further distinguished from 'A7' by its smaller size; fuller growth habit; earlier and more abundant branching; smaller leaf blades with more truncate (less cordate) bases; greener peduncles; smaller spathes with shorter, less aristate tips.

I claim:

1. A new and distinct cultivar of Anthurium plant named 'A4', substantially as described and illustrated herein, characterized particularly as to novelty by its medium to large size; relatively full growth habit; vigorous growth; early and abundant branching; early, year—round and abundant flowering; thick, dark green leaves; relatively large, bright red, very glossy, long—lasting spathes with sharply contrasting light colored spadixes carried on strong peduncles slightly above foliage.

* * * * *